United States Patent
Hoshino

(10) Patent No.: US 8,591,405 B2
(45) Date of Patent: Nov. 26, 2013

(54) BENDING OPERATION DEVICE FOR ENDOSCOPE AND THE ENDOSCOPE

(75) Inventor: Yuki Hoshino, Atsugi (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/480,535

(22) Filed: May 25, 2012

(65) Prior Publication Data

US 2012/0277535 A1 Nov. 1, 2012

Related U.S. Application Data

(63) Continuation of application No. PCT/JP2011/073107, filed on Oct. 6, 2011.

(30) Foreign Application Priority Data

Nov. 25, 2010 (JP) .................................. 2010-262756

(51) Int. Cl.
*A61B 1/00* (2006.01)

(52) U.S. Cl.
USPC .......................................... 600/146; 600/148

(58) Field of Classification Search
USPC ................ 600/146–150, 585; 604/95.04, 528
See application file for complete search history.

(56) References Cited

U.S. PATENT DOCUMENTS

| | | | | |
|---|---|---|---|---|
| 4,461,282 A | * | 7/1984 | Ouchi et al. | 600/148 |
| 5,507,717 A | | 4/1996 | Kura et al. | |
| 2001/0034472 A1 | | 10/2001 | Fujii et al. | |
| 2001/0037051 A1 | | 11/2001 | Fujii et al. | |
| 2009/0076330 A1 | * | 3/2009 | Ashida | 600/146 |

FOREIGN PATENT DOCUMENTS

| | | |
|---|---|---|
| JP | 07-194519 | 8/1995 |
| JP | 09-038027 | 2/1997 |
| JP | 09-038028 | 2/1997 |
| JP | 10-286220 | 10/1998 |
| JP | 2002-034892 | 2/2002 |
| JP | 2005-160791 | 6/2005 |

OTHER PUBLICATIONS

Extended Supplementary European Search Report dated Aug. 9, 2013 issued in corresponding Application No./Patent No. 11843038.8—1660 / 2606811 PCT/JP2011073107.

* cited by examiner

*Primary Examiner* — Katherine Dowe
*Assistant Examiner* — Aaron B Fairchild
(74) *Attorney, Agent, or Firm* — Scully, Scott, Murphy & Presser, P.C.

(57) ABSTRACT

A bending operation device includes a bending operation knob, a friction plate, two tabular fastening members, an annular member including a cam groove for moving the two tabular members from a first position to a second position, and a fixing lever configured to actuate the annular member.

10 Claims, 8 Drawing Sheets

BENDING OPERATION DEVICE FOR ENDOSCOPE AND THE ENDOSCOPE

CROSS REFERENCE TO RELATED APPLICATION

This application is a continuation application of PCT/JP2011/073107 filed on Oct. 6, 2011 and claims benefit of Japanese Application No. 2010-262756 filed in Japan on Nov. 25, 2010, the entire contents of which are incorporated herein by this reference.

BACKGROUND OF THE INVENTION

1. Field of the Invention

The present invention relates to a bending operation device for an endoscope provided in an operation section of the endoscope that bends a bending portion provided in an insertion portion of the endoscope and to the endoscope.

2. Description of the Related Art

In recent years, endoscopes are widely used in a medical field and an industrial field. With the endoscope used in the medical field, it is possible to observe organs in a body cavity, which is an object to be examined, by inserting an elongated insertion portion into the body cavity and to perform various kinds of treatment according to necessity using a treatment instrument inserted into an insertion channel for the treatment instrument included in the endoscope.

With the endoscope used in the industrial field, it is possible to perform observations of scratches, corrosions, and the like of a region to be examined in an object to be examined such as inside a jet engine or piping of a factory and inspections such as various kinds of treatment by inserting an elongated insertion portion of the endoscope into the object to be examined.

A configuration is well known in which a bending portion bendable in plural directions is provided in the insertion portion of the endoscope. The bending portion improves progress properties of the insertion portion in a bent portion in a conduit. Besides, the bending portion changes, in the insertion portion, an observation direction of an observation optical system provided at a distal end portion located further on a distal end side in an inserting direction than the bending portion.

Usually, plural bending pieces are coupled along an inserting direction of the insertion portion, whereby the bending portion provided in the insertion portion of the endoscope is configured to be bendable, for example, in up, down, left, and right four directions. Any one of four wires inserted through the insertion portion, a distal end of which is fixed to the bending piece located most on the distal end side in the inserting direction among the bending pieces, is dragged by a bending operation device provided in an operation section, whereby the bending portion is bendable in any one of the up, down, left, and right directions.

Specifically, the bending portion has a configuration in which a bending operation knob for up and down bending provided in the operation section is operated to pivot, whereby a sprocket for up and down bending provided in the operation section is caused to pivot, and one of an upper chain region and a lower chain region of a chain for up and down bending wound around the sprocket is dragged, whereby the bending portion is bent in an up or down direction.

Further, the bending portion has a configuration in which a bending operation knob for left and right bending provided in the operation section is operated to pivot, whereby a sprocket for left and right bending provided in the operation section is caused to pivot, and one of a left chain region and a right chain region of a chain for left and right bending wound around the sprocket is dragged, whereby the bending portion is bent in a left or right direction.

A configuration is also well known in which the operation section is provided with a lock lever for up and down that fixes a bending angle of the bending portion bent in the up direction or the down direction by the pivoting operation of the bending operation knob for up and down bending, i.e., a pivoting position of the bending operation knob for up and down bending and a lock knob for left and right that fixes a bending angle of the bending portion bent in the left direction or the right direction by the pivoting operation of the bending operation knob for left and right bending, i.e., a pivoting position of the bending operation knob for left and right bending. The configuration is disclosed in, for example, Japanese Patent Application Laid-Open Publication No. 10-286220.

Japanese Patent Application Laid-Open Publication No. 10-286220 discloses a configuration in which a friction member that comes into contact with an inner circumferential surface of the knob and a movable member and a fixed member that can hold the friction member are provided in a space in the bending operation knob for up and down bending. The movable member is fixed to the lock lever for up and down.

When the pivoting position of the bending operation knob for up and down bending is fixed using the configuration disclosed in Japanese Patent Application Laid-Open Publication No. 10-286220, the lock lever for up and down is rotated in one direction and the movable member is rotated in one direction together with the lock lever, whereby the movable member is moved with respect to the fixed member using a screw mechanism, and the friction member is held between the fixed member and the movable member to elastically deform the friction member and the friction member is brought into contact with the inner circumferential surface of the bending operation knob for up and down bending using a friction force, whereby the pivoting position of the bending operation knob for up and down bending is fixed by the friction force.

In Japanese Patent Application Laid-Open Publication No. 10-286220, a configuration for fixing the pivoting position of the bending operation knob for left and right bending has a configuration same as the configuration for fixing the pivoting position of the bending operation knob for up and down bending.

The present invention has been devised in view of the circumstances explained above and it is an object of the present invention to provide a bending operation device for an endoscope including a configuration that can surely fix, with an operation force smaller than that in the past, a pivoting position of a bending operation knob without variations every time the bending operation device is used and provide the endoscope.

SUMMARY OF THE INVENTION

A bending operation device for an endoscope according to an aspect of the present invention is a bending operation provided in an operation section of the endoscope and configured to bend a bending portion of the endoscope including: a bending operation knob configured to pivot about a pivoting shaft to cause the bending portion to perform a bending action; a friction plate including a first surface and a second surface and configured to pivot according to pivoting of the bending operation knob; two tabular members including a first tabular member provided on the first surface side of the friction plate and a second tabular member provided on the second surface side of the friction plate; a moving portion configured to move the first tabular member or the second tabular member from a first position where the two tabular members are separated by a first space from each other to a second position where the two tabular members are separated by a second space shorter than the first space from each other and hold the friction plate therebetween; and a moving portion operation member configured to actuate the moving portion and move the first tabular member or the second tabular member from the first position to the second position.

DETAILED DESCRIPTION OF THE PREFERRED EMBODIMENT

An embodiment of the present invention is explained below with reference to the drawings. It should be noted that the drawings are schematic and relations between thicknesses and widths of respective members, ratios of the thicknesses of the respective members, and the like are different from real ones. It goes without saying that portions having different relations and ratios of dimensions thereof among the drawings are included.

Figure 1:
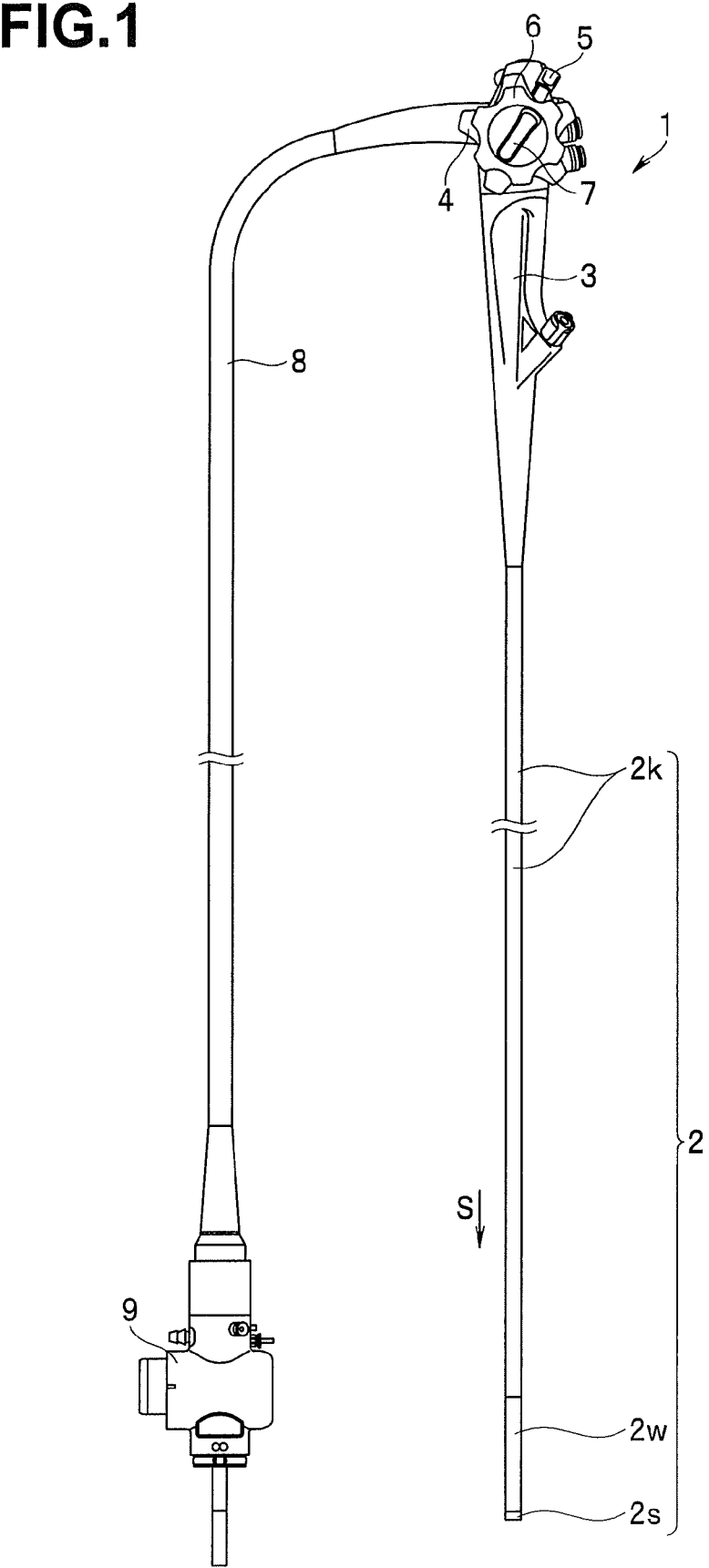
FIG. 1 is a diagram showing an external appearance of an endoscope including, in an operation section, a bending operation device according to the present embodiment.

FIG. 1 is a diagram showing an external appearance of an endoscope including a bending operation device according to the present embodiment in an operation section.

As shown in FIG. 1, a main part of an endoscope 1 is configured to include an insertion portion 2 inserted into an object to be examined, an operation section 3 connected to a proximal end side in an inserting direction S of the insertion portion 2, a universal cord 8 extended from the operation section 3, and a connector 9 provided at an extension end of the universal cord 8. The endoscope 1 is electrically connected to an external apparatus such as a control apparatus or a lighting apparatus via the connector 9.

The operation section 3 is provided with a bending operation knob for up and down (hereinafter simply referred to as bending operation knob) 4 that bends a bending portion 2w explained below of the insertion portion 2 in an up and down direction and a bending operation knob for left and right (hereinafter simply referred to as bending operation knob) 6 that bends the bending portion 2w in a left and right direction.

Further, the operation section 3 is provided with a fixing lever 5, which is a bending operation mechanism actuation lever, that fixes a pivoting position of the bending operation knob 4 and a fixing knob 7 that fixes a pivoting position of the bending operation knob 6.

The bending operation knob 4, the fixing lever 5, the bending operation knob 6, and the fixing knob 7 configure, in conjunction with other members provided in the operation section 3, a bending operation device 100 (see FIG. 2) explained below in the present embodiment.

The insertion portion 2 is configured by a distal end portion 2s, the bending portion 2w, and a flexible tube portion 2k and formed to be elongated along the inserting direction S.

In the distal end portion 2s, a not-shown image pickup unit that observes an inside of the object to be examined, a lighting unit that lights the inside of the object to be examined, and the like are provided.

The bending portion 2w is bent in, for example, up, down, left, and right four directions according to pivoting operation of the bending operation knob 4 and the bending operation knob 6 to thereby change an observing direction of the image pickup unit provided in the distal end portion 2s and improve insertability of the distal end portion 2s in the object to be examined. Further, the flexible tube portion 2k is connected to a proximal end side of the bending portion 2w.

Next, a configuration of the bending operation device 100 for the endoscope provided in the operation section 3 is explained with reference to FIGS. 2 to 10.

Figure 2:
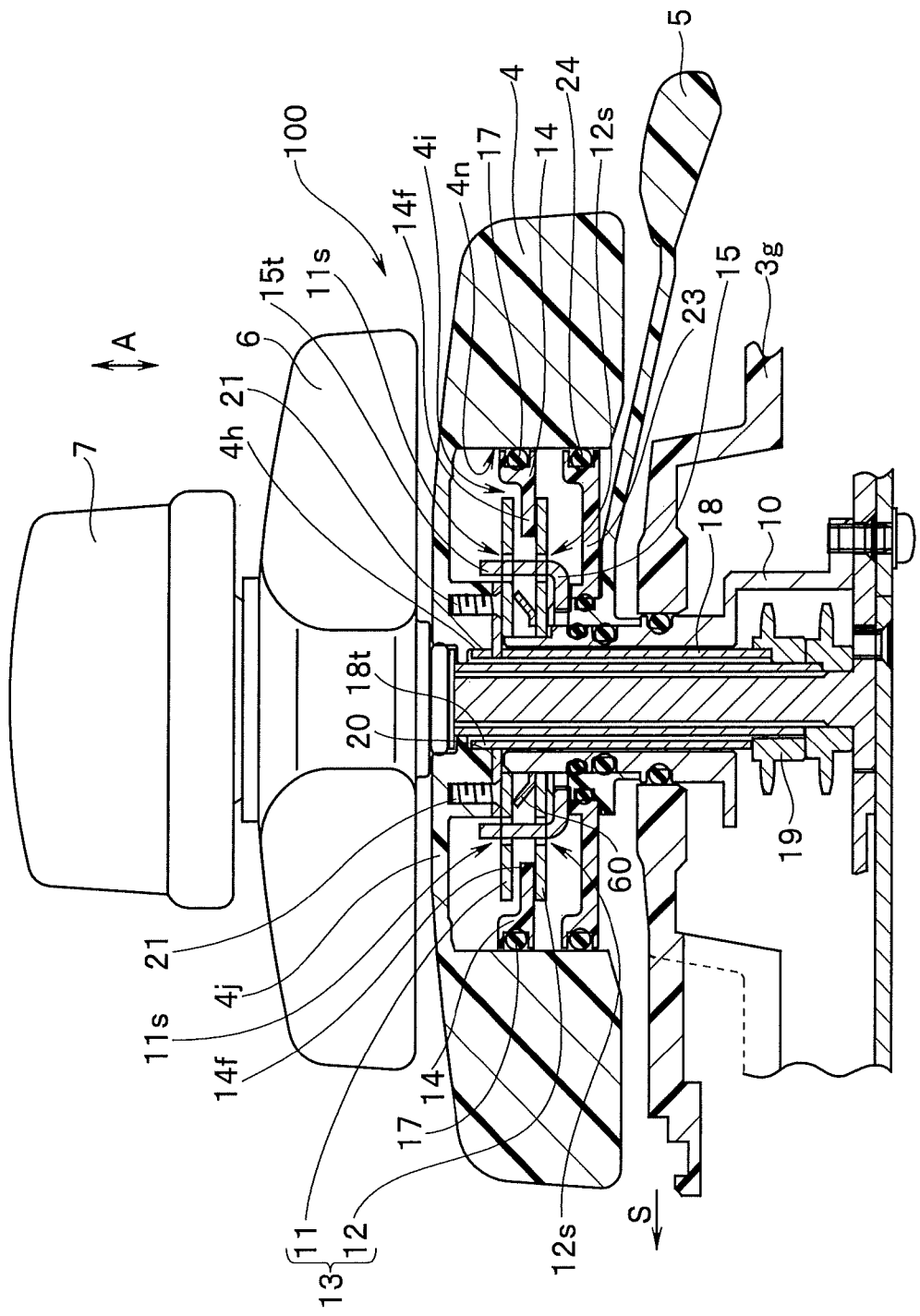
FIG. 2 is a partial sectional view showing a configuration of the bending operation device provided in the operation section of the endoscope shown in FIG. 1.
Figure 3:
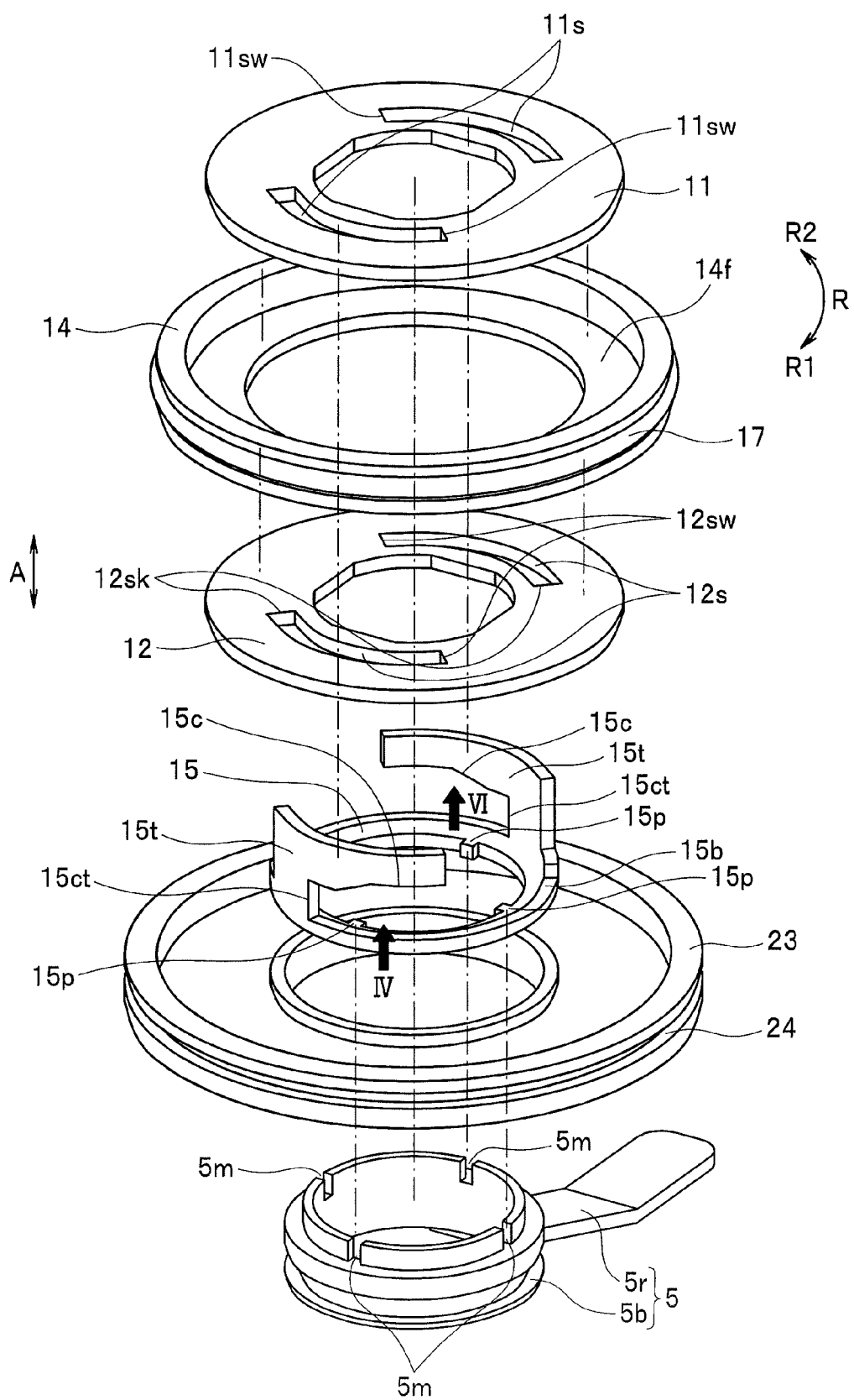
FIG. 3 is an exploded perspective view showing a configuration of two tabular fastening members, a friction plate, an annular member, a support plate, and a fixing lever shown in FIG. 2.

FIG. 2 is a partial sectional view showing the configuration of the bending operation device provided in the operation section of the endoscope shown in FIG. 1. FIG. 3 is an exploded perspective view showing a configuration of the two tabular fastening members, the friction plate, the annular member, the support plate, and the fixing lever shown in FIG. 2.

Figure 4:
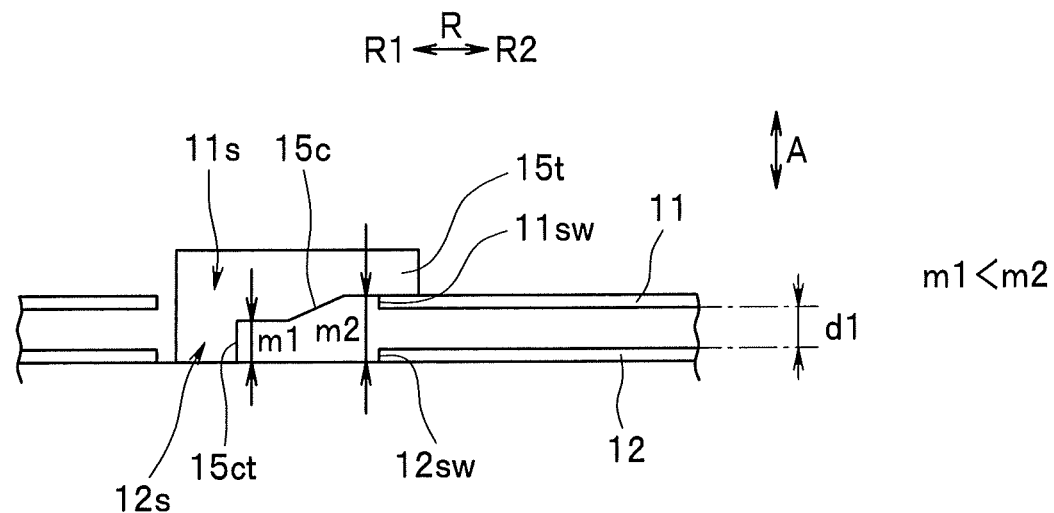
FIG. 4 is a diagram in plan view from a direction of IV in FIG. 3 of a state in which a part of the two tabular fastening members are assembled to fit in, while having a first space therebetween, in a tabular fastening member moving portion provided in a projecting portion of the annular member shown in FIG. 3.
Figure 5:
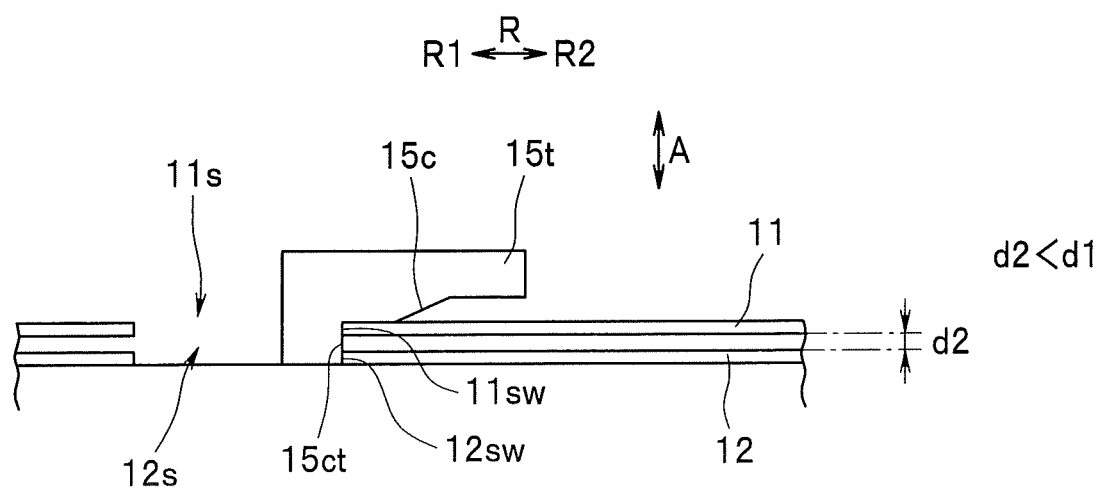
FIG. 5 is a diagram schematically showing in plan view a state in which the two tabular fastening members shown in FIG. 4 are moved to a second space by the tabular fastening member moving portion according to rotation of the annular member.

FIG. 4 is a diagram in plan view from a direction of IV in FIG. 3 of a state in which a part of the two tabular fastening members are assembled to fit in, while having a first space therebetween, in a tabular fastening member moving portion provided in a projecting portion of the annular member shown in FIG. 3. FIG. 5 is a diagram schematically showing in plan view a state in which the two tabular fastening members shown in FIG. 4 are moved to a second space by the tabular fastening member moving portion according to rotation of the annular member.

Figure 6:
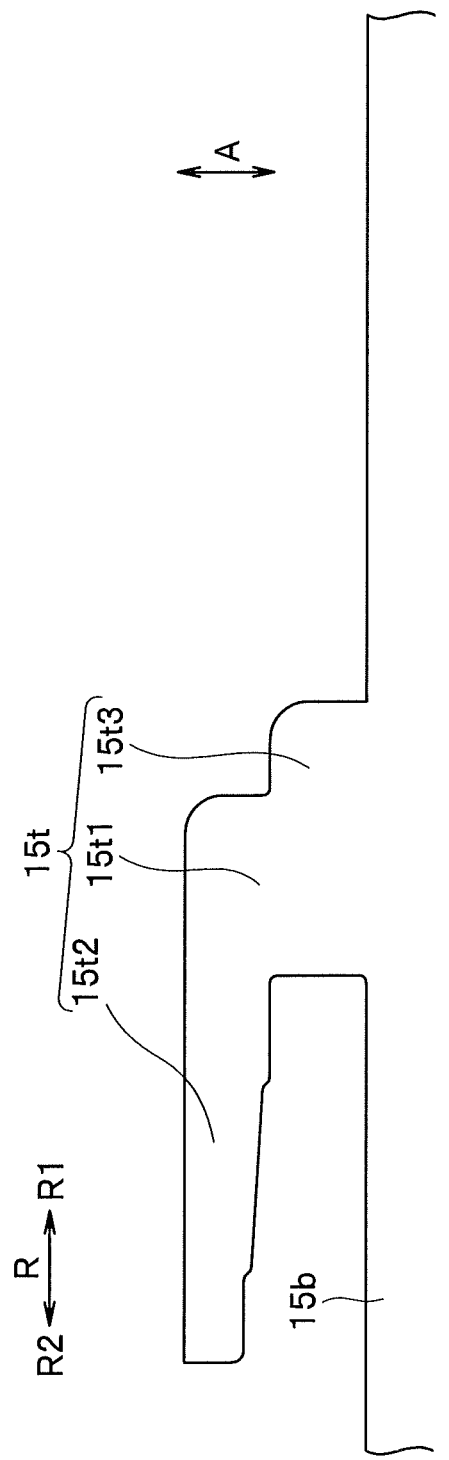
FIG. 6 is a diagram in plan view from the direction of VI in FIG. 3 of the projecting portion of the annular member shown in FIG. 3.
Figure 7:
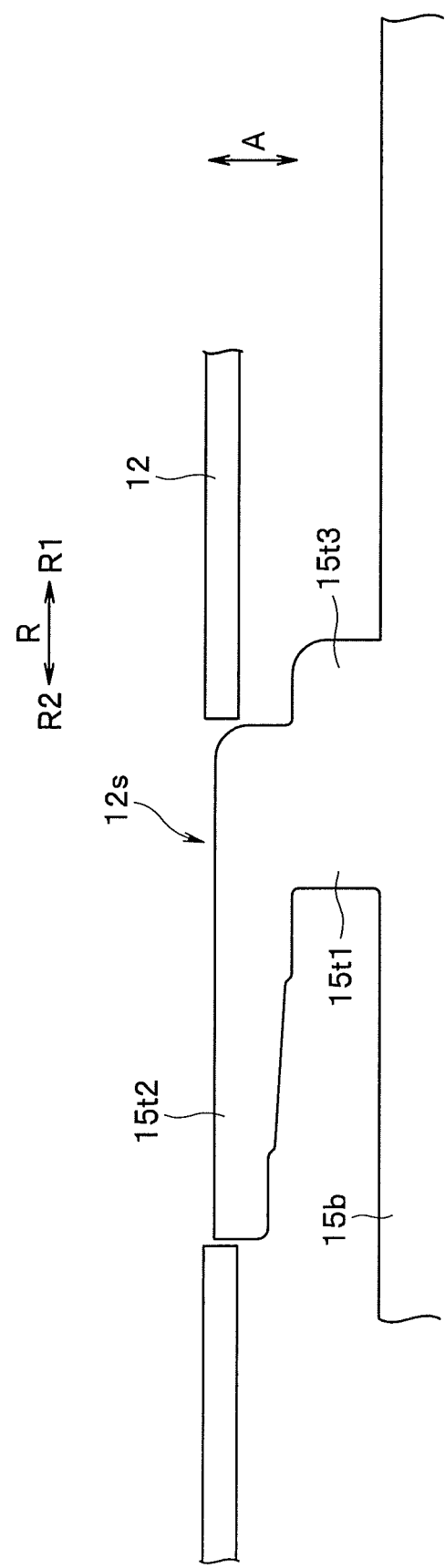
FIG. 7 is a diagram schematically showing in plan view a state in which a traversing region in the projecting portion of the annular member shown in FIG. 6 passes a slit of one tabular fastening member.

Further, FIG. 6 is a diagram in plan view from the direction of VI in FIG. 3 of the projecting portion of the annular member shown in FIG. 3. FIG. 7 is a diagram schematically showing in plan view a state in which a traversing region in the projecting portion of the annular member shown in FIG. 6 passes a slit of one tabular fastening member.

Figure 8:
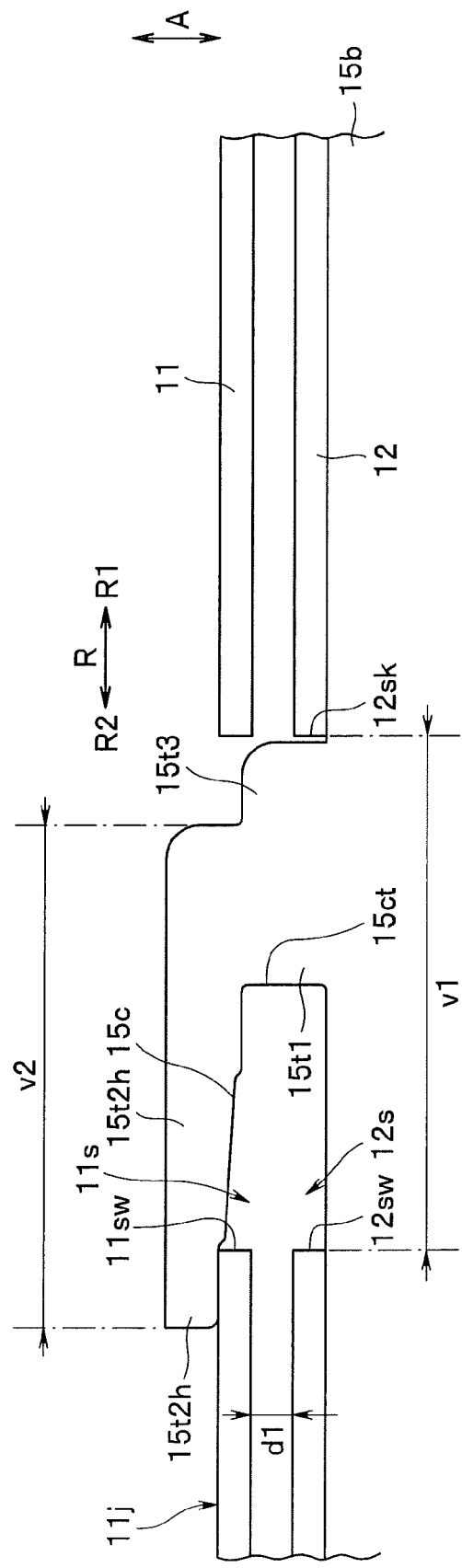
FIG. 8 is a diagram schematically showing in plan view a slip-out prevention state in which the traversing region of the projecting portion shown in FIG. 7 passes slits of the two tabular fastening members, a stepped portion of the projecting portion comes into contact with an opening end of the slit of one tabular fastening member, and a part of the traversing region comes into contact with an upper surface of the other tabular fastening member.

FIG. 8 is a diagram schematically showing in plan view a slip-out prevention state in which the traversing region of the projecting portion shown in FIG. 7 passes slits of the two tabular fastening members, a stepped portion of the projecting portion comes into contact with an opening end of the slit of one tabular fastening member, and a part of the traversing region comes into contact with an upper surface of the other tabular fastening member.

Figure 9:
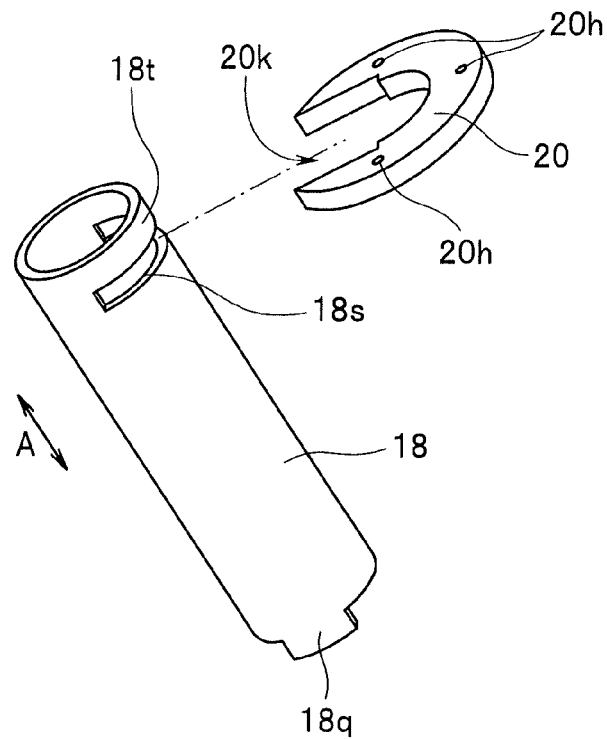
FIG. 9 is a perspective view showing a pivoting shaft member and a tabular fixed member shown in FIG. 2.
Figure 10:
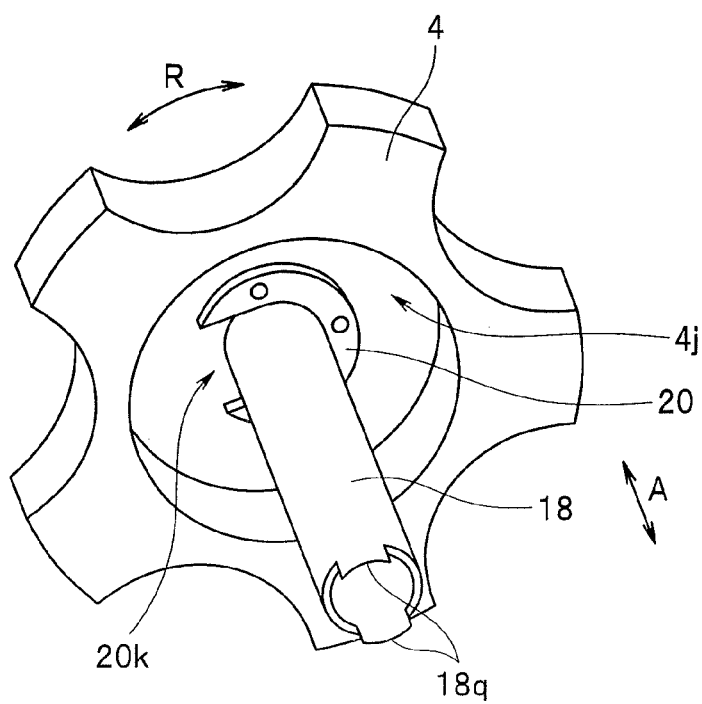
FIG. 10 is a perspective view schematically showing a state in which the tabular fixed member is fit in a slit of the pivoting shaft member shown in FIG. 9 and the tabular fixed member is fixed to a bending operation knob for up and down.

FIG. 9 is a perspective view showing a pivoting shaft member and a tabular fixed member shown in FIG. 2. FIG. 10 is a perspective view schematically showing a state in which the tabular fixed member is fit in a slit of the pivoting shaft member shown in FIG. 9 and the tabular fixed member is fixed to the bending operation knob for up and down.

The configuration of the bending operation device 100 explained below is explained with reference to a configuration related to the bending operation knob 4 and the fixing lever 5 as an example.

As shown in FIG. 2, the bending operation knob 4 is fixed to a cylindrical driving member 18, which is a pivoting shaft member, provided to extend along an axis direction A, which is a direction substantially orthogonal to the inserting direction S, from an inside of the operation section 3. The bending operation knob 4 is rotatable in one direction R1 or the other direction R2 in a pivoting direction R together with the cylindrical driving member 18.

Specifically, as shown in FIG. 2, the bending operation knob 4 has a space 4i on an inside thereof and has a bottomed hole 4h in a pivoting center position of the bending operation knob 4 on an inner surface on the space 4i side on an upper surface 4j on the bending operation knob 6 side in FIG. 2. An extension end 18t of the cylindrical driving member 18 inserted through the space 4i is fit in the hole 4h.

A diameter of the extension end 18t is formed substantially the same as a diameter of the hole 4h. Therefore, a pivoting center of the bending operation knob 4 and a pivoting center of the cylindrical driving member 18 are highly accurately matched by the hole 4h.

Since the extension end 18t of the cylindrical driving member 18 is fit in the hole 4h, movement in a radial direction of the cylindrical driving member 18 with respect to the bending operation knob 4 is prevented.

Further, as shown in FIG. 9, a slit 18s is formed further on the operation section 3 side in the axis direction A than the extension end 18t of the cylindrical driving member 18. As shown in FIG. 10, a cutout 20k of a tabular fixed member 20 formed in a C shape can fit in the slit 18s.

As shown in FIG. 2, the tabular fixed member 20 is fixed to the upper surface 4j of the bending operation knob 4 by screws 21 inserted via plural through-holes 20h formed to pierce through the tabular fixed member 20 in the axis direction A.

Consequently, the cylindrical driving member 18 is fixed to the bending operation knob 4 via the tabular fixed member 20. Pivoting of the cylindrical driving member 18 in the pivoting direction R with respect to the bending operation knob 4 is fixed by the cutout 20k of the tabular fixed member 20. In other words, the cylindrical driving member 18 is configured to pivot integrally with the bending operation knob 4 without pivoting separately from the bending operation knob 4.

The tabular fixed member 20 is formed from a general-purpose inexpensive tabular member by, for example, press working, with which the tabular fixed member 20 can be inexpensively manufactured. The cylindrical driving member 18 is also inexpensively formed from a general-purpose inexpensive cylindrical member with the slit 18s, which can be easily machined, and a projecting portion 18q explained below (see FIG. 9) simply formed therein.

Specifically, in the present embodiment, with a simple and inexpensive configuration in which the extension end 18t further extending than the slit 18s of the cylindrical driving member 18 is only fit in the hole 4h and the inexpensive tabular fixed member 20 fit in the slit 18s of the inexpensive cylindrical driving member 18 is only fixed to the upper surface 4j of the bending operation knob 4 using the screws 21, when the cylindrical driving member 18 is fixed to the bending operation knob 4, it is possible to highly accurately match the pivoting center of the bending operation knob 4 and the pivoting center of the cylindrical driving member 18.

In the past, a flange section is formed at the extension end of the cylindrical driving member 18 and the flange section is fixed to the upper surface 4j. Therefore, it is difficult to highly accurately match the pivoting center of the bending operation knob 4 and the pivoting center of the cylindrical driving member 18. The flange section and the upper surface 4j also have to be formed by cutting work having high machining accuracy. Therefore, there is a problem in that machining costs are high. However, with the configuration of the present embodiment, as explained above, it is possible to inexpensively and highly accurately match the pivoting center of the bending operation knob 4 and the pivoting center of the cylindrical driving member 18.

As shown in FIGS. 9 and 10, the projecting portion 18q is formed at an end of the cylindrical driving member 18 located on the inside of the operation section 3. The projecting portion 18q fits in a sprocket 19 provided on the inside of the operation section 3. A not-shown chain for bending the bending portion 2w is wound around the sprocket 19.

Consequently, when the bending operation knob 4 is operated to rotate in one direction R1 or the other direction R2, the cylindrical driving member 18 fixed to the bending operation knob 4 also rotates in the same direction as the bending operation knob 4 and the sprocket 19 rotates in the same direction. Therefore, any one side of the chain is dragged, whereby the bending portion 2w bends in the up or down direction.

A combination of the sprocket 19 and the chain is not a limitation. A configuration may be adopted in which the projecting portion 18q is fit in a pulley and a wire wound around the pulley is dragged according to rotation of the pulley.

Referring back to FIG. 2, a cylindrical pivoting stop member 10 extending from the inside of the operation section 3 along the axis direction A is provided in an outer circumference of the cylindrical driving member 18 with an extending region of the pivoting stop member 10 inserted through a space 4i on an inside of the bending operation knob 4.

The pivoting stop member 10 is fixed to an armor member 3g of the operation section 3 via an O ring or the like and located in a radial direction while having a predetermined space from the cylindrical driving member 18. Therefore, the pivoting stop member 10 is configured not to pivot with respect to the cylindrical driving member 18.

The fixing lever 5 formed of, for example, resin located in the space 4i on the inside of the bending operation knob 4 is set in contact with an outer circumference of the pivoting stop member 10 via an O ring or the like to be pivotable in the pivoting direction R.

Specifically, as shown in FIG. 3, an annular portion 5b of the fixing lever 5 including a grasping portion 5r and the annular portion 5b as shown in FIG. 3 is set in contact with the outer circumference of the pivoting stop member 10 via an O ring or the like to be pivotable in the pivoting direction R.

An inner circumferential surface of a support plate 23 located in the space 4i on the inside of the bending operation knob 4 is set in contact with an outer circumference of the annular portion 5b of the fixing lever 5 via an O ring or the like. An outer circumferential surface of the support plate 23 is set in contact with an inner circumferential surface 4n of the bending operation knob 4 via an O ring 24 or the like.

Further, in the outer circumference of the pivoting stop member 10, further on the upper surface 4j side than the annular portion 5b of the fixing lever 5, an annular member 15 formed of, for example, metal located in the space 4i on the inside of the bending operation knob 4 is located coaxially with the fixing lever 5 in the axis direction A.

As shown in FIG. 3, a main part of the annular member 15 is configured to include an annular base 15b and two projecting portions 15t projecting from the base 15b to the upper surface 4j side in the axis direction A to be opposed to each other.

Plural convex portions 15p projecting from the base 15b in an inner circumferential direction respectively fit in plural concave portions 5m formed on a surface on the annular member 15 side of the annular portion 5b of the fixing lever 5, whereby the annular member 15 is fixed to the fixing lever 5.

This means that the annular member 15 can rotate in one direction R1 or the other direction R2 of the pivoting direction R together with the fixing lever 5 according to the fitting of the convex portions 15p in the concave portions 5m. In other words, the fixing lever 5 performs pivoting operation of the annular member 15. The annular member 15 and the fixing lever 5 are prevented from pivoting together with the cylindrical driving member 18 by the pivoting stop member 10.

As shown in FIG. 3, the projecting portions 15t of the annular member 15 have a partial arcuate shape along the pivoting direction R. As shown in FIG. 6, a main part of the projecting portion 15t is configured to include an erected region 15t1 projecting to the upper surface 4j side in the axis direction A, a traversing region 15t2 extending from a projecting end of the erected region 15t1 in the other direction R2, and a stepped portion 15t3.

In the projecting portion 15t, a cam groove 15c, which is a tabular fastening member moving portion, is formed along the pivoting direction R between the base 15b and the traversing region 15t2 in the axis direction A. A detailed configuration of the cam groove 15c is explained below.

Referring back to FIG. 2, in the outer circumference of the pivoting stop member 10, further on the upper surface 4j side than the base 15b of the annular member 15, one tabular fastening member 11 and the other tabular fastening member 12 formed of, for example, metal located coaxially with the annular member 15 in the axis direction A and located in the space 4i on the inside of the bending operation knob 4 are respectively fixed.

Since the respective tabular fastening members 11 and 12 are fixed to the pivoting stop member 10, the tabular fastening members 11 and 12 are configured not to pivot with respect to the cylindrical driving member 18 together with the pivoting stop member 10.

A friction plate 14 formed of, for example, resin located coaxially with the two tabular fastening members 11 and 12 in the axis direction A and located in the space 4i on the inside of the bending operation knob 4 is provided between the two tabular fastening members 11 and 12 in the axis direction A.

In the friction plate 14, an O ring 17, which is an elastic body, provided on an outer circumferential surface is set in contact with the inner circumferential surface 4n of the bending operation knob 4 with a shape and a pressing amount set in advance such that a proper bending retaining force is obtained with respect to the bending operation knob 4. In a second position explained below (see FIG. 5), the friction plate 14 includes a flange section 14f held between the two tabular fastening members 11 and 12 in the axis direction A.

The O ring 17 may be discontinuously set in contact with the inner circumferential surface 4n. The friction plate 14 pivots together with the bending operation knob 4 in a first position explained below (see FIG. 4).

As shown in FIG. 3, in the tabular fastening members 11 and 12, in predetermined superimposing positions in a state of the tabular fastening members 11 and 12 in plan view, for example, from the upper surface 4j side in the axis direction A, slits 11s and 12s having a partial arcuate shape are respectively formed in the pivoting direction R to pierce through the tabular fastening members 11 and 12 in the axis direction A.

As shown in FIG. 8, width v1 in the pivoting direction R of the slits 11s and 12s is formed in width substantially the same as width v2 in the pivoting direction R of the traversing region 15t2 in the projecting portion 15t of the annular member 15 or slightly larger than the width v2.

The projecting portions 15t of the annular member 15 are inserted through the respective slits 11s and 12s to be movable in one direction R1 or the other direction R2 in the pivoting direction R.

Specifically, as shown in FIG. 7, after the traversing region 15t2 is caused to pass the slit 12s of the tabular fastening member 12 from the base 15b side in the axis direction A, the projecting portion 15t of the annular member 15 is tilted and the traversing region 15t2 is caused to further pass the slit 11s of the tabular fastening member 11. Then, as shown in FIG. 8, the tabular fastening member 12 comes into contact with the base 15b of the annular member 15, the stepped portion 15t3 of the projecting portion 15t comes into contact with an opening end 12sk of the slit 12s, and a distal end 15t2h of the traversing region 15t2 comes into contact with an upper surface 11j of the tabular fastening member 11.

In other words, in a state in which the projecting portion 15t of the annular member 15 is inserted through the respective slits 11s and 12s, a part of the two tabular fastening members 11 and 12 are fit in cam grooves 15c.

The projecting portion 15t can move in the slits 11s and 12s in the pivoting direction to a position where the stepped portion 15t3 comes into contact with the opening end 12sk and a position where ends 11sw and 12sw explained below (see FIG. 8) of the two tabular fastening members 11 and 12 come into contact with an end 15ct of the cam groove 15c explained below.

When the stepped portion 15t3 is in contact with the opening end 12sk, as shown in FIGS. 4 and 8, the two tabular fastening member 11 and 12 are separated from each other while having a first space d1 therebetween in the axis direction A by a spring 60, which is a fixing release member, provided between the tabular fastening members 11 and 12 shown in FIG. 2. In the following explanation, a position where the tabular fastening members 11 and 12 are separated from each other by the first space d1 in the axis direction A is referred to as first position.

In the first position, as shown in FIG. 8 referred to above, the distal end 15t2h of the traversing region 15t2 of the projecting portion 15t in the annular member 15 is in contact with the upper surface 11j of the tabular fastening member 11. Therefore, the projecting portion 15t does not come off the respective slits 11s and 12s to the operation section 3 side. In other words, the traversing region 15t2 and the stepped portion 15t3 of the projecting portion 15t configure a slip-out preventing portion that prevents the projecting portion 15*t* from slipping out of the respective slits 11*s* and 12*s*.

Further, when the stepped portion 15*t*3 of the projecting portion 15*t* of the annular member 15 is in contact with the opening end 12*sk* in the first position shown in FIG. 4, as shown in FIG. 8, the projecting portion 15*t* of the annular member 15 is regulated from rotating in one direction R1 with respect to the slit 12*s*.

As explained above, the cam groove 15*c* is formed in the projecting portion 15*t* in the pivoting direction R.

Specifically, as shown in FIG. 4, the cam groove 15*c* is formed having an inclined surface or an arcuate surface such that a groove space in the axis direction A decreases from m2 to m1 smaller than m2 (m2>m1) toward one direction R1.

Therefore, when the annular member 15 is rotated in the other direction R2 from the first position, the projecting portion 15*t* moves in the other direction R2 in the slits 11*s* and 12*s* until the ends 11*sw* and 12*sw* of the slits 11*s* and 12*s* of the tabular fastening members 11 and 12 come into contact with the end 15*ct* in the pivoting direction R of the cam groove 15*c*.

According to the movement, the tabular fastening member 11 is guided with respect to the tabular fastening member 12 by the inclined surface or the arcuate surface formed in the cam groove 15*c* and torque is converted into a force in the axis direction A. Consequently, as shown in FIG. 5, in the axis direction A, the tabular fastening member 11 moves, resisting an urging force of the spring 60, to a second position where the tabular fastening member 11 is separated from the tabular fastening member 12 while having a second space d2 shorter than the first space d1 (d2<d1) therebetween.

In other words, the cam groove 15*c* has a shape for moving the tabular fastening member 11 from the first position to the second position according to rotation in the other direction R2 of the annular member 15. The cam groove 15*c* has a function of converting torque into a force in the axis direction A and moving the tabular fastening member 11 from the first position to the second position according to the rotation in the other direction R2 of the annular member 15.

The cam groove 15*c* may be formed in a shape for moving not only the tabular fastening member 11 but also both the tabular fastening members 11 and 12 from the first position to the second position.

In the second position shown in FIG. 5, the flange section 14*f* of the friction plate 14 is held by the tabular fastening members 11 and 12, whereby pivoting of the friction plate 14 that pivots together with the bending operation knob 4 is fixed. The O ring 17 comes into contact with the inner circumferential surface 4*n* of the bending operation knob 4 with a friction force.

A pivoting position of the bending operation knob 4 is fixed by the friction force. At this point, a force for holding the flange section 14*f* with the tabular fastening members 11 and 12 is larger than the friction force of the bending operation knob 4 and the O ring 17.

Even in a state in which the O ring 17 is in contact with the inner circumferential surface 4*n* with the friction force, when the bending operation knob 4 is rotated in one direction R1 or the other direction R2 by a force larger than the friction force of the O ring 17 against the inner circumferential surface 4*n*, the bending operation knob 4 can pivot even if the flange section 14*f* is held by the two tabular fastening members 11 and 12.

When the annular member 15 is rotated in one direction R1 opposite to the other direction R2 in the second position shown in FIG. 5, the projecting portion 15*t* moves in the slits 11*s* and 12*s* until the stepped portion 15*t*3 shown in FIG. 8 comes into contact with the opening end 12*sk* of the slit 12*s*.

In this case, the tabular fastening member 11 is moved to the first position shown in FIG. 4 by the spring 60 rather than the shape of the cam groove 15*c*. In this state, since the flange section 14*f* is not held between the tabular fastening members 11 and 12, the bending operation knob 4 and the friction plate 14 can pivot.

Consequently, in the space 4*i* on the inside of the bending operation knob 4, the tabular fastening members 11 and 12 can move, in the axis direction A, according to the pivoting of the fixing lever 5, to the first position where the tabular fastening members 11 and 12 are separated from each other while having the first space d1 therebetween and the second position where the tabular fastening members 11 and 12 are separated from each other while having the second space d2 therebetween.

In the bending operation device 100, a configuration concerning the bending operation knob 6 and the fixing knob 7 is the same configuration except that the fixing lever 5 is replace with the fixing knob 7 and the bending operation knob 4 is replaced with the bending operation knob 6. Therefore, explanation of the configuration is omitted.

Next, action of the present embodiment is briefly explained.

First, when the bending portion 2 of the insertion portion 2 is bent in the up or down direction, an operator rotates the bending operation knob 4 in one of one direction R1 and the other direction R2 in the pivoting direction R.

In this case, since the two tabular fastening members 11 in the bending operation knob 4 are located in the first position shown in FIG. 4 where the tabular fastening members 11 and 12 do not hold the flange section 14*f* of the friction plate 14, the O ring 17 provided on the outer circumferential surface of the friction plate 14 is simply in contact with the inner circumferential surface 4*n* of the bending operation knob 4. Therefore, since the friction plate 14 pivots together with the bending operation knob 4, the operator can easily rotate the bending operation knob 4 in one direction R1 or the other direction R2.

As a result, the cylindrical driving member 18 and the sprocket 19 fixed to the bending operation knob 4 also rotate in one direction R1 or the other direction R2, whereby any one side of the chain wound around the sprocket 19 is dragged. Consequently, the bending portion 2*w* is bent in the up or down direction. In this case, the pivoting stop member 10 does not pivot because the pivoting stop member 10 is configured not to pivot with respect to the cylindrical driving member 18.

Subsequently, when the operator desires to fix a bending angle in the up or down direction of the bending portion 2*w* by the pivoting operation of the bending operation knob 4, i.e., when the operator desires to fix a pivoting position of the bending operation knob 4, the operator rotates the fixing lever 5 in the other direction R2 with respect to the pivoting stop member 10. As a result, the annular member 15 also rotates in the other direction R2. In this case, the pivoting stop member 10 and the two tabular fastening members 11 and 12 fixed to the pivoting stop member 10 do not rotate in the other direction R2.

As a result, in the slits 11*s* and 12*s* of the two tabular fastening members 11 and 12, the projecting portion 15*t* of the annular member 15 moves in the other direction R2 in the slits 11*s* and 12*s* until the ends 11*sw* and 12*sw* of the slits 11*s* and 12*s* of the tabular fastening members 11 and 12 come into contact with the end 15*ct* of the cam groove 15*c*.

Consequently, the tabular fastening member 11 is guided with respect to the tabular fastening member 12 by the inclined surface or the arcuate surface formed in the cam groove 15c. Torque is converted into a force in the axis direction A. As shown in FIG. 5, in the axis direction A, the tabular fastening member 11 moves, resisting the urging force of the spring 60, to the second position where the tabular fastening member 11 is separated from the tabular fastening member 12 while having the second space d2 shorter than the first space d1 therebetween.

Thereafter, in the second position, the flange section 14f of the friction plate 14 is held between the tabular fastening members 11 and 12. Therefore, the O ring 17 comes into contact with the inner circumferential surface 4n of the bending operation knob 4 with a friction force. A pivoting position of the bending operation knob 4 is fixed by the friction force.

Even in a state in which the O ring 17 comes into contact with the inner circumferential surface 4n of the bending operation knob 4 with the friction force, when the bending operation knob 4 is rotated in one direction R1 or the other direction R2 with a force larger than the friction force of the O ring 17 against the inner circumferential surface 4n, the bending operation knob 4 can pivot.

Next, when the operator desires to release the fixing of the pivoting position of the bending operation knob 4, the operator rotates the fixing lever 5 in one direction R1 with respect to the pivoting stop member 10. Therefore, the annular member 15 also rotates in one direction R1.

As a result, in the second position shown in FIG. 5, the projecting portion 15t moves in the slits 11s and 12s until the stepped portion 15t3 shown in FIG. 8 comes into contact with the opening end 12sk of the slit 12s. The tabular fastening member 11 is moved to the first position shown in FIG. 4 by the spring 60 explained above. In this state, since the flange section 14f is not held between the tabular fastening members 11 and 12, the flange section 14f can pivot together with the friction plate 14. Therefore, the fixing of the pivoting position of the bending operation knob 4 is released.

As explained above, in the present embodiment, the two tabular fastening members 11 and 12 provided on the inside of the bending operation knob 4 are moved from the first position to the second position in the axis direction A using the cam groove 15c provided in the projecting portion 15t of the annular member 15 that rotates in the other direction R2 together with the fixing lever 5 according to the rotation in the other direction R2 of the fixing lever 5. The flange section 14f of the friction plate 14 is held between the two tabular fastening members 11 and 12 in the second position and the O ring 17 provided on the outer circumferential surface of the friction plate 14 is brought into contact with the inner circumferential surface 4n of the bending operation knob 4 with a friction force, whereby the pivoting of the bending operation knob 4 is fixed.

Consequently, even if the fixing lever 5 is operated to rotate with a small force, the flange section 4f of the friction plate 14 can be held with a large force by the two tabular fastening members 11 and 12 using the cam groove 15c. Therefore, a fixing force in a pivoting position in the bending operation knob 4 can be increased.

The pivoting of the bending operation knob 4 can be fixed by a simple configuration for holding the flange section 4f between the two tabular fastening members 11 and 12. Further, a friction force applied from the O ring 17 to the bending operation knob 4 can be specified simply by specifying three elements, i.e., a diameter of the O ring 17, an inner diameter of the bending operation knob 4, and an outer diameter of the friction plate 14. In other words, the number of component members that generate the friction force is small. Therefore, variations rarely occur in the friction force.

Unlike the past, it is unnecessary to elastically deform plural times a member that comes into contact with the inner circumferential surface 4n of the bending operation knob 4 and fixes the pivoting of the bending operation knob 4. Therefore, the O ring 17 is not deteriorated by the plural times of the elastic deformation. Therefore, it is possible to surely fix the pivoting of the bending operation knob without variations every time the bending operation device 100 is used.

Further, the configuration of the present embodiment can be realized simply by adding the two tabular fastening members 11 and 12 and the annular member 15 to the configuration of the bending operation device 100 in the past. Therefore, it is possible to realize a reduction in the number of components, a reduction in assembly man-hour, and a reduction in costs.

Consequently, it is possible to provide the bending operation device 100 for an endoscope including a configuration that can surely fix the pivoting of the bending operation knob 4 without variations with an operation force smaller than that in the past every time the bending operation device 100 is used.

In the present embodiment, the two tabular fastening members 11 and 12 are moved in the axis direction A from the first position to the second position according to the rotation of the fixing lever 5 using the cam groove 15c provided in the projecting portion 15t of the annular member 15. However, the cam groove is not a limitation. It goes without saying that the two tabular fastening members 11 and 12 may be moved in the axis direction A from the first position to the second position by a screw mechanism or the like according to the rotation of the fixing lever 5.

What is claimed is:

1. A bending operation device provided in an operation section of an endoscope and configured to bend a bending portion of the endoscope, the bending operation device comprising:

a bending operation knob configured to pivot about a pivoting shaft to cause the bending portion to perform a bending action;

a friction plate including a first surface and a second surface and configured to pivot according to pivoting of the bending operation knob;

two tabular members including a first tabular member provided on the first surface side of the friction plate and a second tabular member provided on the second surface side of the friction plate;

slits respectively formed in the two tabular members to pierce through the two tabular members in a direction of the pivoting shaft in a predetermined superimposed position in a state of the two tabular members in plan view from a direction coaxial with the pivoting shaft;

a moving portion configured to move the first tabular member or the second tabular member from a first position where the two tabular members are separated by a first space from each other to a second position where the two tabular members are separated by a second space shorter than the first space from each other and hold the friction plate therebetween to thereby fix a pivoting position of the bending operation knob;

a moving portion operation member configured to actuate the moving portion and move the first tabular member or the second tabular member from the first position to the second position; and an annular member including the moving portion, the annular member including a projecting portion configured to pierce through the respective slits of the two tabular members in an axis direction of the pivoting shaft and move in the respective slits in a direction of the pivoting, and pivoting about the pivoting shaft separately from the pivoting of the pivoting shaft when the moving portion operation member is operated to pivot the annular member.

2. The bending operation device according to claim 1, wherein
the moving portion is a cam groove provided in the annular member in which the two tabular members are fit and moves in the pivoting direction with respect to the two tabular members, and
the cam groove has a shape for moving the two tabular members from the first position to the second position according to rotation of the annular member.

3. The bending operation device according to claim 2, wherein the cam groove has a shape in which a groove space in the axis direction of the pivoting shaft decreases along the pivoting direction toward the pivoting direction in which the two tabular members move from the first position to the second position.

4. The bending operation device according to claim 3, wherein a slip-out preventing portion that prevents the projecting portion from slipping out of the respective slits of the two tabular members is provided in the projecting portion of the annular member.

5. The bending operation device according to claim 1, wherein the moving portion moves, in the two tabular members, one of the tabular members with respect to the other of the tabular members in the axis direction of the pivoting shaft from the first position to the second position.

6. The bending operation device according to claim 5, wherein the moving portion moves the first tabular member located in a space on an inside of the bending operation knob from the first position to the second position with respect to the second tabular member.

7. The bending operation device according to claim 1, wherein
the friction plate includes a flange section held between the two tabular members in the second position and includes an elastic body provided on an outer circumference of the friction plate and set in contact with the inner circumferential surface of the bending operation knob, and
the two tabular members hold the flange section in the second position, whereby the elastic body comes into contact with the inner circumferential surface of the bending operation knob with a friction force to thereby fix a pivoting position of the bending operation knob.

8. The bending operation device according to claim 1, wherein a fixing release member that moves the two tabular members from the second position to the first position is provided between the two tabular members in an axis direction of the pivoting shaft.

9. The bending operation device according to claim 1, further comprising a pivoting stop member to which the bending operation knob is fixed, the pivoting stop member being provided so as to be separated from the pivoting shaft in a radial direction of the pivoting shaft and configured not to pivot with respect to the pivoting shaft, wherein
the two tabular members are fixed to an outer circumference of the pivoting stop member.

10. An endoscope comprising the bending operation device for the endoscope according to claim 1, the bending operation device being provided in the operation section.

* * * * *